United States Patent [19]

Miyata et al.

[11] Patent Number: 5,177,062
[45] Date of Patent: Jan. 5, 1993

[54] METHOD FOR TREATING IMMUNE COMPLEX DISEASES WITH N-ACETYLNEURAMINIC ACID

[75] Inventors: Takeshi Miyata; Kazuo Takahama; Hirofumi Kai, all of Kumamoto; Takayuki Ishii, Tokyo; Keiji Komatsu, Tokorozawa, all of Japan

[73] Assignee: MECT Corporation, Tokyo, Japan

[21] Appl. No.: 325,649

[22] Filed: Mar. 20, 1989

[30] Foreign Application Priority Data

Aug. 9, 1988 [JP] Japan ............................. 63-198598
Mar. 8, 1989 [JP] Japan ............................. 1-55562

[51] Int. Cl.⁵ ............................................ A61K 31/70
[52] U.S. Cl. ........................................ 514/23; 514/42; 514/62
[58] Field of Search .................. 514/23, 62; 536/53, 536/18.7

[56] References Cited

U.S. PATENT DOCUMENTS

| | | | |
|---|---|---|---|
| 4,663,443 | 5/1987 | Shibayama et al. | 536/53 X |
| 4,762,822 | 8/1988 | Ettinger | 514/25 |
| 4,774,326 | 9/1988 | Shibayama et al. | 536/53 X |
| 4,797,477 | 1/1989 | Yoshimura et al. | 536/53 X |

FOREIGN PATENT DOCUMENTS

| | | |
|---|---|---|
| 273388 | 6/1988 | European Pat. Off. |
| 3624816 | 5/1987 | Fed. Rep. of Germany ........ 514/23 |
| 43-16042 | 6/1968 | Japan ................. 514/23 |
| 283990 | 9/1986 | Japan ................. 536/53 |
| 221694 | 9/1987 | Japan ................. 536/53 |
| 63-44589 | 2/1988 | Japan . |
| 63-222192 | 9/1988 | Japan . |

OTHER PUBLICATIONS

Roy et al., Carbohydrate Research, 177, C1-C4 (1988).

Ogasaware et al., Chemical Abstracts, 106, 144004j (1987).
Jensen et al., Chemical Abstracts, 106, 174469g (1987).
Schauer, "Sialic Acids and Their Role as Biological Masks", Trends Biochem. Sci. (Pers. Ed)., 10(a), pp. 357-360 (1985).
Czezowska, et al., Chemical Abstracts, 68, 27294q (1968).
Czezowska, et al., Chemical Abstracts, 66, 9519e (1967).
Ivanitskii, Chemical Abstracts, 77, 135884b (1972).
Mnapakanyan, et al., Chemical Abstracts, 83, 204711f (1975).
The Merck Manual of Diagnosis and Therapy, fifteenth edition, (1987) pp. 318-319, 1274-1277 and 1588-1595.

Primary Examiner—Johnnie R. Brown
Assistant Examiner—Elli Peselev
Attorney, Agent, or Firm—Rodman & Rodman

[57] ABSTRACT

A preparation for treating immune complex diseases which comprises injection containing the following compound:

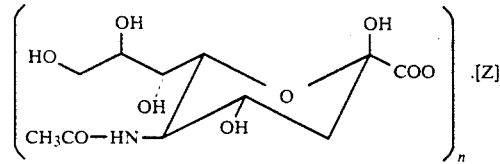

wherein when n is 1, Z represents a hydrogen, lithium, potassium, sodium, ammonium or organic ammonium, and when n is 2, Z represents calcium, barium or magnesium, as an active ingredient and pharmacologically acceptable carrier. The preparation of the present invention may be used in any administration method such as hypodermic, intramuscular and intravenous.

7 Claims, 2 Drawing Sheets

METHOD FOR TREATING IMMUNE COMPLEX DISEASES WITH N-ACETYLNEURAMINIC ACID

BACKGROUND OF THE INVENTION

1. Field of the Invention

This invention relates to a preparation for treating immune complex diseases, more particularly to a preparation containing N-acetylneuraminic acid as an effective substance.

2. Related Art Statement

The term "antiallergic agent" has been used to describe a compound which inhibits disengagement or production of chemical mediators against allergic reactions, particularly the type I allergic reaction.

As the reasons, there have been considered that (1) among the allergic reaction, those which can be seen in many cases are the type I allergic reaction, (2) histamine disengagement which is one of the main mediators of the type I can be caused also in the type II or III, and histamine is one of the most important factors which modify the type IV reaction, and (3) for therapy of diseases due to the other type II, III or IV allergic reaction, steroids have often been used.

Among the allergic reactions other than the type I, the type III allergic reaction is classified into an immediate allergy as in the type I allergic reaction, and is an allergic inflammation reaction which is participated in an antigen-antibody complex (immune complex), a complement and a polymorphonuclear leukocyte (mainly neutrophils).

As a representative disease, there may be mentioned systemic lupus erythematosus (SLE), complex glomerular nephritis, serum disease, etc., but since the type III allergic reaction is called Arthus reaction as a byname, the representative experimental model is referred to as the Arthus reaction.

The Arthus reaction is an inflammation reaction which can be observed particularly on the skin as edema and bleeding, and its main reaction sequence includes (1) sedimentation of immune complex at vessel wall and surrounding tissues, (2) activation of complement system through classical pathway (partially, through the alternative pathway), (3) aggregation of polymorphonuclear leukocytes to a reaction site, (4) immune adhesion of polymorphonuclear leukocytes to materials and cells in which C3b is coated thereon, (5) reinforcement of phagocytosis of polymorphonuclear leukocytes, (6) release of lysosomal enzyme from polymorphonuclear leukocytes, and (7) disorder of cells (erythrocytes, etc.) and tissues.

In vivo, a material which combines with heteropolysaccharides in various ways and carries biological functions as an important constituent for the heteropolysaccharides, is sialic acid.

With regard to the biological functions of sialic acid in an immune system, research has reported that it shows specific antigenic properties, is an essential component for the receptor molecule, and exhibits antirecognition effects that mask the immune recognition site.

These effects can be obtained with a bound type sialic acid. As the reason, there may be considered that (1) in conventional research on the biological function of the sialic acid, special attention has been given to how the physiological activity of the substrate is influenced by removing the sialic acid bound to heteropolysaccharides (particularly the cell membrane) with sialidase, or by effecting modification such as periodate oxidation, etc., (2) it is difficult to quantitatively analyze sialic acid since the amount of free type sialic acid present in blood is minute.

In recent years, it has been reported that N-acetylneuraminic acid which is one of the most representative sialic acids shows antiviral effect or anti-inflammatory effect [(1) Lobert L. Hess, et al., The Journal of Immunology, vol. 127, No. 5 (1981), pp. 1740-1743; (2) P. Gorog, et al., Agents and Actions, vol 8, No. 5 (1978), pp. 543-545; (3) Hiromi Ito, et al., Pharmacology and Therapy, vol. 13, No. 7 (1985), pp. 479-494, et al].

However, little is know about the physiological properties, particularly the pathophysiological properties of N-acetylneuraminic acid, and pharmacological investigation has been inadequate.

BRIEF DESCRIPTION OF THE DRAWINGS

In the accompanying drawings, FIGS. 1 and 2 schematically show experimental test results for the intradermal administration of the inventive preparation in treating immune complex diseases characterized by an Arthus type inflammatory response.

SUMMARY OF THE INVENTION

Figure 1:
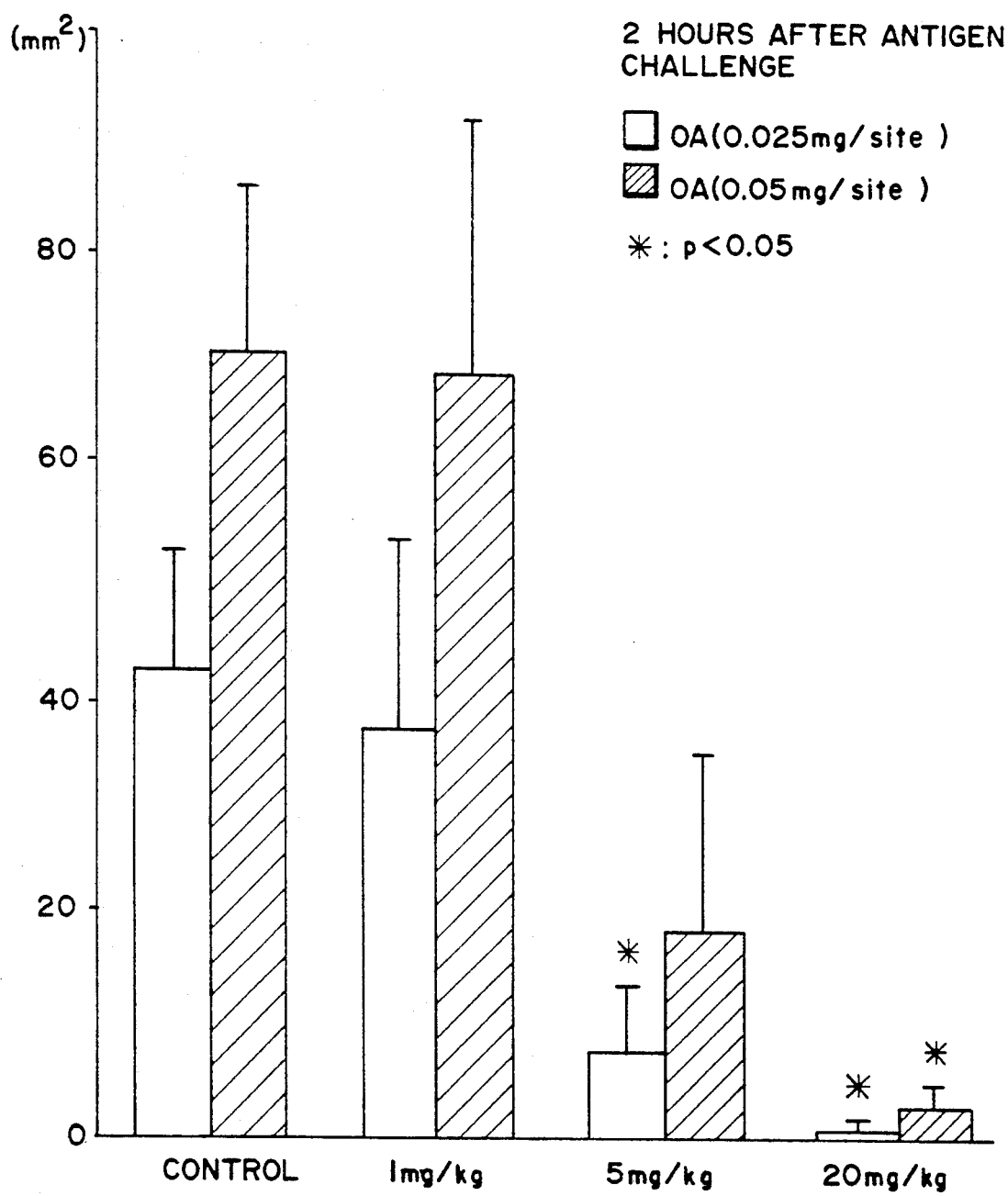

The present inventors have investigated the pharmacological effect of sialic acid for a long time, and have found that N-acetylneuraminic acid which is a representative compound thereof has an inhibiting effect to type I allergic reaction, has an inhibiting effect against an increase in the amount of histamine in bronchial anaphylaxis, and has inhibitory effect against an increase in the amount of leukotriene due to exposure to sulfite gas.

Further, the present inventors have found that the N-acetylneuraminic acid has inhibiting effect also to type III allergic reaction (Arthus reaction).

An object of the present invention is to provide a preparation for treating immune complex disease containing the following compound:

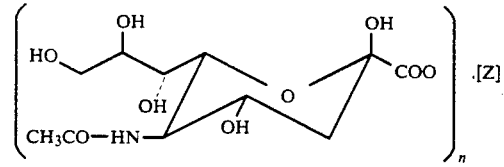

wherein when n is 1, Z represents a hydrogen, lithium, potassium, sodium, ammonium or organic ammonium, and when n is 2, Z represents calcium, barium or magnesium, as an active ingredient.

The preparation of the present invention may be used in any administration method such as hypodermic, intramuscular and intravenous, and an amount thereof is suitably 0.1 to 10.0% by weight. Since N-acetylneuraminate is most stable at a pH range of 5.0 to 6.5 and is little effected by an ionic strength, it is possible to use it with conventional additives generally used in an injection and not limited thereby. In the following description, examples of prescription for preparation are mentioned, but in addition to them, it is possible to alter or combinedly use it with buffers, isotonic agents, excipients, stabilizers, pH adjusters, preservatives, etc. (collectively referred to as "carrier") and the present invention is not limited to the following examples of prescription.

The above and other objects, and novel characteristic feature of the present invention will be more clarified by the following Examples.

DETAILED DESCRIPTION OF THE PREFERRED EMBODIMENTS

In the following, function and effects of the compounds of the present invention will be described by referring to the examples.

EXAMPLE 1

Function of the agent to be tested against PCA (Passive Cutaneous Anaphylaxis) reaction (1) Animal for Experiment Male Hartley guinea pig weighing 300 to 400 g was used.

(2) Experimental Material

Anti-OA IgG (rabbit) (antibody value = 1/36000 or higher) was used as antiserum and OA (Ovalbumin) was used as an antigen. As a stain solution to be added into an antigen solution, 1% Evans blue was used. As the agent to be tested, the sodium salt of N-acetylneuraminic acid (available from MECT Corporation) was used.

(3) Experimental Method

A guinea pig was intradermally administered with 0.1 ml of 16000-fold or 8000-fold diluted antiserum, and after 4 hours, an antigen solution in which 2 ml of 1% Evans blue was added to 10 ml/(1 kg of guinea pig body weight) of the antigen was intravenously injected to cause the PCA reaction. Thereafter, the above guinea pig was killed and after peeling its skin, dye effused area and dye extracted concentration were measured.

Also, before 30 minutes causing the PCA reaction, that is, after 3 hours and 30 minutes from sensitization by the antiserum, an agent to be tested or a physiological saline solution was intravenously administered to guinea pigs of the Groups I to IV as shown below, and functions of the agent to be tested against the PCA reaction were investigated. Six guinea pigs were used for each group.

Group I: 1 mg/(1 kg of guinea pig body weight) of sodium N-acetylneuraminate was administered.

Group II: 5 mg/(1 kg of guinea pig body weight) of sodium N-acetylneuraminate was administered.

Group III: 20 mg/(1 kg of guinea pig body weight) of sodium N-acetylneuraminate was administered.

Group IV: 1 ml/(1 kg of guinea pig body weight) of physiological saline solution was administered.

(4) Results

TABLE 1

| I (KI-111 1 mg/kg) | 1/16000 | 73.3 |
|---|---|---|
|  | 1/8000 | 79.8 |
| II (KI-111 5 mg/kg) | 1/16000 | 13.5 |
|  | 1/8000 | 28.6 |
| III (KI-111 20 mg/kg) | 1/16000 | 49.2 |
|  | 1/8000 | 45.0 |

TABLE 2

| I (KI-111 1 mg/kg) | 1/16000 | 127.5 |
|---|---|---|
|  | 1/8000 | 83.5 |
| II (KI-111 5 mg/kg) | 1/16000 | 51.5 |
|  | 1/8000 | 27.8 |
| III (KI-111 20 mg/kg) | 1/16000 | 41.0 |

TABLE 2-continued

| | 1/8000 | 44.7 |
|---|---|---|

Tables 1 and 2 show dye effused area and dye extracted concentration of each Group of I to III. The numerals are calculated based on the data of Group IV (physiological saline solution administered group) as 100.

As shown in Tables 1 and 2, in Group I to III, inhibition of dye effused area and dye extracted concentration can be observed in both of 16000-fold and 8000-fold antiserum.

(5) Judgment

According to the results of the above PCA reaction, it shows that sodium N-acetylneuraminate has inhibitory effect to type I allergy by pre-administration.

EXAMPLE 2

Function of the agent to be tested against increase of histamine amount due to bronchial anaphylaxis (1) Animal for Experiment Male Hartley guinea pig weighing 300 to 400 g was used.

(2) Experimental Material

Anti-OA IgG (rabbit) was used as antiserum and OA (Ovalubumin) was used as an antigen. As the agent to be tested, sodium salt of N-acetylneuraminic acid (available from MECT Corporation) was used.

(3) Experimental Method

To a guinea pig was intravenously administered 10-fold diluted antiserum so as to become 5 ml per 1 kg of weight, and after 18 hours, 5 mg/ml of an antigen solution was inhaled for 3 minutes to cause bronchial anaphylaxis. Thereafter, the above guinea pig was killed and the histamine amount in BALF (Bronchoalveolar lavage fluid) was measured.

Before 30 minutes of administration of antigen, an agent to be tested or a physiological saline solution was intravenously administered to guinea pigs of the groups of I and II as shown below, effects of the agent to be tested against histamine release was investigated. The guinea pigs were used 8 and 10 for groups I and II, respectively.

Group I: 20 mg/(1 kg of guinea pig body weight) of sodium N-acetylneuraminate was administered.

Group II: 1 ml/(1 kg of guinea pig body weight) of physiological saline solution was administered.

(4) Results

TABLE 3

| | Histamine (ug/ml) |
|---|---|
| I Sodium N-acetylneuraminate | 0.63 |
| II Physiological saline solution | 1.07 |

Table 3 shows average values of histamine levels of Group I and II, respectively. As shown in Table 3, in Group I, increase of histamine levels in BALF can be inhibited.

(5) Judgment

From the above results, it shows that sodium N-acetylneuraminate has inhibitory effect against the increase in histamine levels in bronchial anaphylaxis.

EXAMPLE 3

Function of the agent to be tested against increase in leukotriene levels due to exposure to sulfite gas

(1) Animal for Experiment

Male Wistar rat weighing 180 to 200 g was used.

(2) Experimental Material

As the agent to be tested, sodium salt of N-acetylneuraminic acid (available from MECT Corporation) was used.

(3) Experimental Method

A rat was exposed to 400 ppm of sulfite gas for 4 hours, and after 30 minutes, an agent to be tested or saline solution was inhaled as shown below.

Group I: 300 mg/m$^3$ of sodium N-acetylneuraminate was inhaled for one hour.

Group II: 25 ml of saline solution was inhaled for one hour.

Immediately after completion of inhalation of the agent to be tested or saline solution, and after 4, 8 and 12 hours, rats of each group were killed and the change in levels of leukotriene in BALF was compared and investigated. For each time, 6 rats were used in respective groups.

TABLE 4

|  |  | 0 hr | 4 hr | 8 hr | 12 hr |
|---|---|---|---|---|---|
| I | Sodium | LTB$_4$ | 127.1 | 123.7 | 74.3 | 113.2 |
|   | N-acetyl-neuraminate | LTC$_4$ | 149.1 | 88.8 | 93.5 | 102.0 |
| II | Saline | LTB$_4$ | 326.1 | 241.0 | 288.2 | 281.8 |
|    | solution | LTC$_4$ | 331.7 | 243.5 | 222.9 | 180.1 |

LT: Leukotriene

(4) Results

Table 4 shows change in leukotriene B$_4$ and C$_4$ with a lapse of time of Group I and II. The numerals are calculated on LT value of normal animals as 100.

As shown in Table 4, in Group II, remarkable increases were observed in both leukotriene B$_4$ and C$_4$, but in Group I, changes are both remarkably little in leukotriene B$_4$ and C$_4$.

(5) Judgment

From the above results, it shows that sodium N-acetylneuraminate has a remarkable inhibiting effect to increase in leukotriene levels in rats due to exposure to sulfite gas.

EXAMPLE 4

Effects of N-acetylneuraminate against passive Arthus reaction

(1) Animal for Experiment

Male Hartley guinea pig weighing 300 to 400 g was used.

(2) Preparation of Antiserum (Rabbit Heterocellular Affinity Antiserum)

According to the conventional method, Anti-OA (rabbit) was prepared. That is, by using New Zealand strain rabbits having a weight of 2.0 to 2.2 kg, 1 ml of an emulsion comprising 20 mg of OA and Freund complete adjuvant (available from DIFCO LABORATORIES) was subcutaneously injected to back side portion and active sensitization was effected 4 times for every two weeks.

After two weeks from the final sensitizing date, blood was gathered from common carotid artery and after separation of antiserum, it was stored under freezing at $-20°$ C. for the experiment.

(3) Experimental Method

The passive Arthus reaction was effected according to the method of Katayama et al. [S. Katayama, et al., Arzneim.-Forsch., vol. 31, p. 1196 (1981)]. However, in order, to cause sufficient reaction, a change was made in the concentration of OA solution. That is, sensitization was effected by intravenously injecting 1 ml of antiserum stock solution and 30 minutes after, the reaction was caused by intradermal injection to each one portion of an abdominal part and total two portions of guinea pig at which hair was cut the day before. At this time, a physiological saline solution was intradermally injected simultaneously in the same manner as a blank. After 2 hours and 24 hours of antigen challenge, a diameter of bleeding at each stimulated portion was measured and a square of the diameter was made as an index of a degree of the reaction. And, the value was calibrated by the blank to be made as the experimental results.

1, 5 or 20 mg/kg of sodium N-acetylneuraminate, or saline solution (1 mg/kg) as a control was intravenously injected before 30 minutes of antigen-challenge or immediately after sensitization.

(4) Statistical Treatment

Experiments more than 6 were carried out and the experimental results were shown as an average ± standard deviation. Also, Student's t-test was employed for significant test and $p<0.05$ was made as statistically significant.

Figure 2:
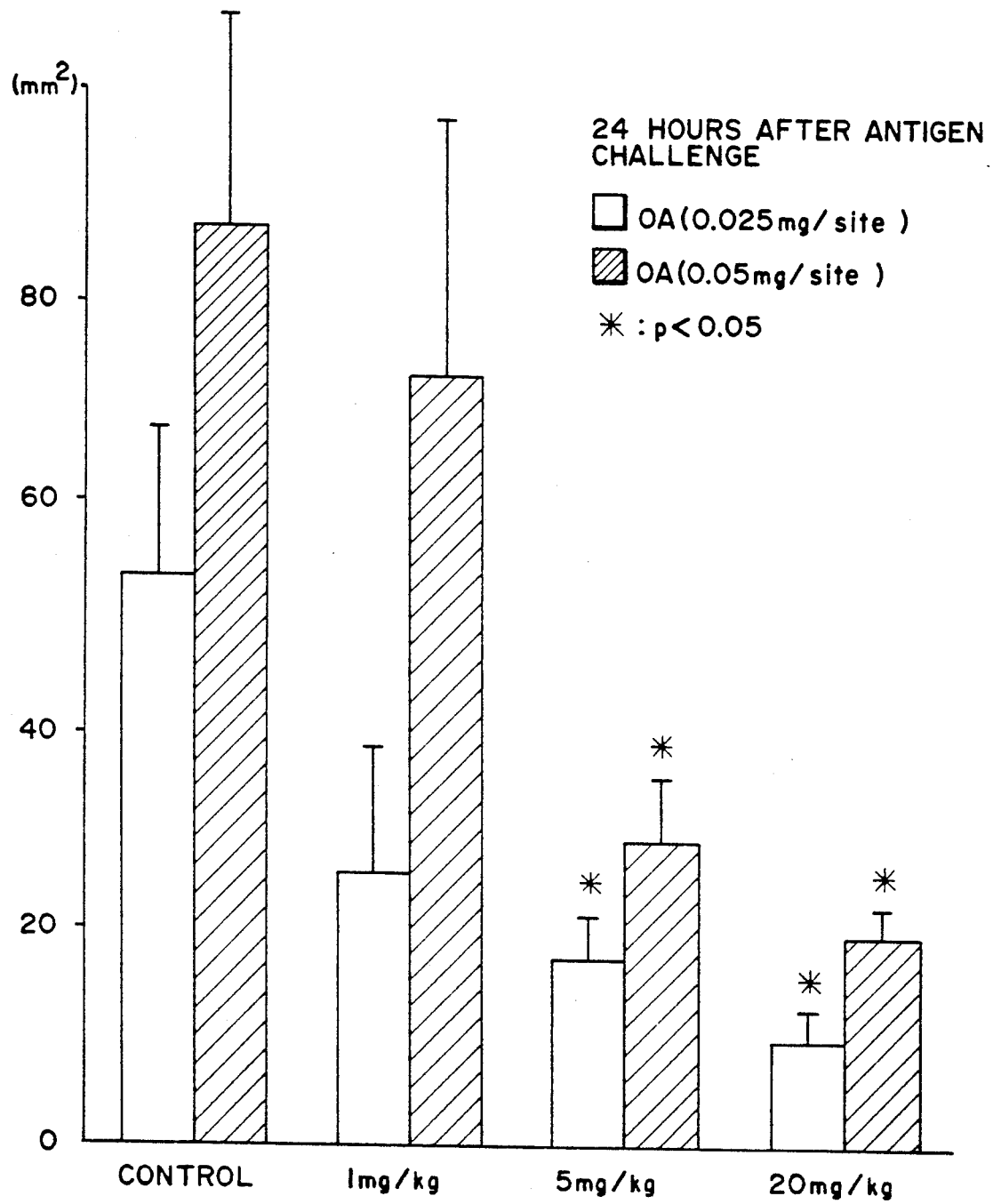

Experimental results are shown in FIG. 1 and FIG. 2.

(5) Results

As clearly seen from FIG. 1 and FIG. 2, by administering sodium N-acetylneuraminate, bleeding of the skin can be depressed depending on the amount to be used, and it is remarkable at 20 mg/kg. Also, this inhibiting effect is continued even after 24 hours from antigen challenge.

EXAMPLE 5

Preparation Example—Water-Soluble Injection

In about 4,000 ml of distilled water were dissolved 10.055 g of acetic acid and 22.79 g of sodium acetate, and 20.0 g of potassium N-acetylneuraminate was added to the solution and the mixture was diluted to 5,000 ml with the addition of distilled water. Next, this solution was filtered through a membrane filter and separately poured in a 5 ml ampul made of a glass. After heat sealing the ampul, sterilization was effected according to the conventional method. This injection contains 20 mg of potassium N-acetylneuraminate in 5 ml.

EXAMPLE 6

Preparation Example 5.0 g of potassium N-acetylneuraminate and 18.0 g of sodium chloride were charged into a vessel and the mixture was diluted to 1,000 ml with addition of distilled water for injection. This solution was filtered through a membrane filter, and separately poured in a vial bottle with each 1 ml. This was lyophilized according to the conventional method by using a lyophilization device to give a lyophilized product. After introduction of nitrogen gas therein, it was stopped with a rubber stopper to give a powder injection which is to be used in solution. This product contains 5 mg of potassium N-acetylneuraminate per one vial and it is to be used by dissolving it in 2 ml of distilled water for injection.

EXAMPLE 7

Preparation Example—Water-Soluble Injection

In about 4,000 ml of distilled water were dissolved 10.055 g of acetic acid and 22.79 g of sodium acetate, and 20.0 g of sodium N-acetylneuraminate was added to the solution and the mixture was diluted to 5,000 ml with the addition of distilled water. Next, this solution was filtered through a membrane filter and separately poured in a 5 ml glass ampul. After heat sealing the ampul, sterilization was effected according to the conventional method. This injection contains 20 mg of sodium N-acetylneuraminate in 5 ml.

EXAMPLE 8

Preparation Example 5.0 g of sodium N-acetylneuraminate and 18.0 g of sodium chloride were charged in a vessel and the mixture was diluted to 1,000 ml with addition of distilled water for injection. This solution was filtered through a membrane filter, and separately poured in a vial bottle with each 1 ml. This was lyophilized according to the conventional method by using a lyophilization device to give a lyophilized product. After introduction of a nitrogen gas therein, it was stopped with a rubber stopper to give a powder injection which is to be used in solution. This product contains 5 mg of sodium N-acetylneuraminate in each vial and it is to be used by dissolving it in 2 ml of distilled water for injection.

EXAMPLE 9

Acute Toxicity Test

Acute toxicity tests of sodium N-acetylneuraminate against mouse, rat and guinea pig due to oral, subcutaneous injection, intraperitoneal injection, intravenous injection and inhalation were effected as shown below.

(1) Animals to be Tested

ICR mouse: 6 weeks old
SD rat: 6 weeks old
Hartley guinea pig: 6 weeks old (2) Chemicals Concentration 20% (w/v): dissolved in distilled water (3) Animal Number Per One Level Ten (4) Terms Observed 14 days (5) Calculation Method of $LD_{50}$ Probit method
The results are shown in Table 5.

TABLE 5

| Acute toxicity test of sodium N-acetylneuraminate | | | | | |
|---|---|---|---|---|---|
| | | $LD_{50}$ (mg/kg) Administration route | | | | |
| Kinds of animal | sex | oral | hypo-dermic | abdo-minal | intra-venous | inhal-ation |
| Mouse | male | >5,000 | >5,000 | >5,000 | >5,000 | — |
| | female | >5,000 | >5,000 | >5,000 | >5,000 | — |
| Rat | male | >5,000 | >5,000 | >5,000 | >5,000 | >4,000 mg/m$^3$ |
| | female | >5,000 | >5,000 | >5,000 | >5,000 | >4,000 mg/m$^3$ |
| Guinea pig | — | — | — | — | >5,000 | — |

Inhalation is effected by spraying the agent to be tested and exposing for one hour.

EXAMPLE 10

Simple Acute Toxicity Test

Simple acute toxicity test of the agent to be tested by intravenous injection into mice was effected as shown below.

1. Experimental Material and Method (1) Agents to be tested
Lithium salt, potassium salt, barium salt and magnesium salt of N-acetylneuraminic acid (all available from MECT Corporation) were used.

(2) Animal for experiment
  ddy male mouse
  Weight at beginning of the test: 17.7 t 21.1 g
  Animal number per one level: 3

(3) Room temperature: 23°±1° C., Humidity: 55+7%

(4) Administration route: intravenous (5) Administration method and amount thereof
The above agent to be tested was dissolved in a physiological saline solution, prepared to become the administration amount of 0.2 ml per 20 g of mouse weight which was injected into a tail vein. The administered amount was made in three levels of 500, 1000 and 2000 mg/kg.

(6) Observation of general condition and death condition

Observations of the general condition and presence or absence of death were conducted immediately after administration to after 7 days.

2. Results (1) Death rate
Death rate was shown in Table 6.
At 1000 and 2000 mg/kg, 3 out of 3 samples died from magnesium salt, barium salt and potassium salt of N-acetylneuraminic acid. At 500 mg/kg, 3 out of 3 samples died from N-acetylneuraminic acid barium salt. Other than the above, no death was observed.

(2) General condition
Died samples were accompanied by clonic convulsion and incontinence of urine and almost all the samples died immediately after administration or within one minute. In the viral samples, inhibition in ultromotivity can be observed in a little sample but recovered within one hour.

TABLE 6

| Agent | Administerd amount mg/kg | 1 | 3 | 6 | 24 | 2 | 3 | 4 | 5 | 6 | 7 | Final death rate |
|---|---|---|---|---|---|---|---|---|---|---|---|---|
| | | hrs | | | | days | | | | | | |
| Lithium N-acetylneuraminate | 500 | 0 | 0 | 0 | 0 | 0 | 0 | 0 | 0 | 0 | 0 | 0/3 |
| | 1000 | 0 | 0 | 0 | 0 | 0 | 0 | 0 | 0 | 0 | 0 | 0/3 |
| | 2000 | 0 | 0 | 0 | 0 | 0 | 0 | 0 | 0 | 0 | 0 | 0/3 |
| Potassium N-acetylneuraminate | 500 | 0 | 0 | 0 | 0 | 0 | 0 | 0 | 0 | 0 | 0 | 0/3 |
| | 1000 | 3 | 0 | 0 | 0 | 0 | 0 | 0 | 0 | 0 | 0 | 3/3 |
| | 2000 | 3 | 0 | 0 | 0 | 0 | 0 | 0 | 0 | 0 | 0 | 3/3 |
| Barium N-acetylneuraminate | 500 | 3 | 0 | 0 | 0 | 0 | 0 | 0 | 0 | 0 | 0 | 3/3 |
| | 1000 | 3 | 0 | 0 | 0 | 0 | 0 | 0 | 0 | 0 | 0 | 3/3 |
| | 2000 | 3 | 0 | 0 | 0 | 0 | 0 | 0 | 0 | 0 | 0 | 3/3 |
| Magnesium N-acetylneuraminate | 500 | 0 | 0 | 0 | 0 | 0 | 0 | 0 | 0 | 0 | 0 | 0/3 |
| | 1000 | 3 | 0 | 0 | 0 | 0 | 0 | 0 | 0 | 0 | 0 | 3/3 |
| | 2000 | 3 | 0 | 0 | 0 | 0 | 0 | 0 | 0 | 0 | 0 | 3/3 |

What is claimed is:

1. A method for treating immune complex diseases characterized by an Arthus type inflammatory response in an animal, which comprises administering to said animal a preparation containing an effective amount of a compound represented by the formula:

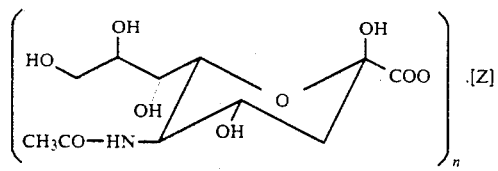

as the active ingredient, wherein when n is 1, Z represents a hydrogen, lithium, potassium, sodium, ammonium or an organic ammonium; and when n is 2, Z represents calcium, barium or magnesium; and a pharmaceutically acceptable carrier.

2. The method of claim 1, wherein the preparation comprises about 0.1 to 10% by weight of the active ingredient.

3. The method of claim 1, wherein the active ingredient is selected from the group consisting of sodium N-acetylneuraminate and potassium N-acetylneuraminate.

4. The method according to claim 1, wherein said preparation is administered by injection means.

5. The method according to claim 4, wherein said injection means is selected from the group consisting of hypodermic, intramuscular and intravenous injections.

6. The method of claim 1, wherein the preparation is made from a powder that is dissolved in solution prior to use.

7. The method of claim 1, wherein the preparation also contains at least one agent as a carrier selected from the group consisting of stabilizers, buffers, isotonic agents, excipients, pH adjusters and preservatives.

* * * * *